(12) United States Patent
Blau (10) Patent No.: US 6,759,477 B2
(45) Date of Patent: Jul. 6, 2004

(54) METHOD FOR PREPARING IMIDES FROM SULFONYL FLUORIDES

(75) Inventor: Hanne Anna Katharina Blau, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 43 days.

(21) Appl. No.: 10/129,168

(22) PCT Filed: Dec. 1, 2000

(86) PCT No.: PCT/US00/32672
§ 371 (c)(1),
(2), (4) Date: May 1, 2002

(87) PCT Pub. No.: WO01/40174
PCT Pub. Date: Jun. 7, 2001

(65) Prior Publication Data
US 2002/0193499 A1 Dec. 19, 2002

Related U.S. Application Data

(60) Provisional application No. 60/168,539, filed on Dec. 2, 1999.

(51) Int. Cl.$^7$ .................................................. C08L 27/12
(52) U.S. Cl. .................... 524/544; 524/551; 524/609; 524/805; 524/834
(58) Field of Search ................................ 524/544, 551, 524/609, 805, 834

(56) References Cited

U.S. PATENT DOCUMENTS

3,282,875 A     11/1966  Connolly et al.
5,463,005 A  *  10/1995  Desmarteau ................ 526/240

FOREIGN PATENT DOCUMENTS

EP           0850920        12/1997
WO        WO 9945048         9/1999

OTHER PUBLICATIONS

Von Johann N. Meubdoerffer und Hans Niederptim, Bisperfluoralkansulfonylimide, Chemiker–Zeitung, (1972) pp. 582–583, vol. 96, Jahrgang.

* cited by examiner

Primary Examiner—William K Cheung

(57) ABSTRACT

This invention discloses a method for preparing imides (I) and (II) from compounds having a sulfonyl fluoride functional group. The imides so prepared are useful in a variety of catalytic and electrochemical applications. (I) or polymer comprising the unit (II)

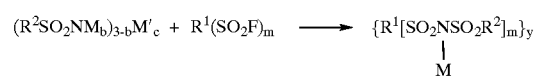

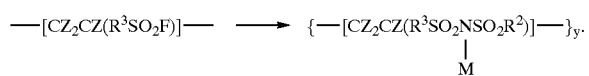

30 Claims, 1 Drawing Sheet

FIG. 1

METHOD FOR PREPARING IMIDES FROM SULFONYL FLUORIDES

This application claims the benefit of Provisional Application No. 60/168,539, filed Dec. 2, 1999.

FIELD OF THE INVENTION

This invention is directed to a method for preparing imides from compounds having a sulfonyl fluoride functional group. The imides so prepared are useful in a variety of catalytic and electrochemical applications.

BACKGROUND OF THE INVENTION

Compounds having a sulfonyl fluoride functional group are well known in the art. In particular, vinyl ethers and olefins having a fluorosulfonyl fluoride group have been found to be particularly useful as monomers for copolymerization with tetrafluoroethylene, ethylene, vinylidene fluoride and other olefinic and fluoroolefinic monomers to form polymers which, upon hydrolysis are converted to highly useful ionomers. One area of important use for ionomers so formed is in the area of lithium batteries. See for example Connolly et all U.S. Pat. No. 3,282,875 and commonly assigned Ser. No. 09/023,244 U.S. Pat. No. 6,025,092 and Ser. No. 09/061,132 U.S. Pat. No. 6,100,324.

It is also known to prepare imides from compounds having sulfonyl fluoride functionality particularly fluorinated organic sulfonyl imides are known in the art. For example, DesMarteau, U.S. Pat. No. 5,463,005, discloses substituted perfluoro-olefins of the formula where X=CH or N, Z=H, K, Na, or Group I or II metal, R=one or more fluorocarbon groups including fluorocarbon ethers and/or sulfonyl groups and/or perfluoro non-oxy acid groups, Y=perfluoroal or F, and m=0 or 1.

Xue, Ph.D. thesis, Clemson University, 1996, discloses the formation of the monomer $$CF_2=CF-OCF_2CF_2SO_2N(Na)SO_2CF_3$$

by reaction of $CF_2=CF-OCF_2CF_2SO_2Cl$ with $CF_3SO_2NHNa$ in the presence of $Na_2CO_3$ in acetonitrile. However, Xue's method is not applicable to the sulfonyl fluoride species without first protecting the double bond.

Further disclosed by Xue, op.cit, is $CF_3SO_2NNa_2$ made by combining $CF_3SO_2NHNa$ and NaH in THF and reacting for four hours at room temperature. The inventors hereof have determined that Xue's method of preparation provides a conversion of less than 10% from $CF_3SO_2NHNa$ to $CF_3SO_2NNa_2$. No method of separation is provided, nor is any method provided for preparing the $CF_3SO_2NNa_2$ at higher yield. Thus no means is provided for producing $CF_3SO_2NNa_2$ in a highly purified state. Xue suggests that $CF_3SO_2NNa_2$ can be reacted with a cyclic sulfone of the formula:

to produce the vinyl ether monomer, $CF_2=CF-OCF_2CF_2SO_2N(Na)SO_2CF_3$. Also disclosed by Xue is a reaction between $CF_2=CFOCF_2CF_2SO_2F$ and $CF_3SO_2NHNa$ to produce an unusable complex mixture of products. Xue makes no suggestion that $CF_3SO_2NNa_2$ is effective at converting sulfonyl fluoride containing compounds to imides.

MeuBdoerffer et al., Chemiker Zeitung, 96. Jahrgang (1972) No. 10, 582–583 discloses a method for synthesizing $RSO_2NH_2$ wherein R is perfluoroalkyl.

Feiring et al., WO 9945048(A1), provides a method for imidizing fluorinated vinyl ether monomers containing a sulfonyl fluoride group by first protecting the double bond and then converting the sulfonyl fluoride into an imide.

Armand et al, EPO 0 850 920 A2, discloses a method for imidizing sulfonyl fluoride and chloride species containing aromatic rings.

SUMMARY OF THE INVENTION

The present invention provides for a process comprising: Contacting, in a liquid dispersion or solution, a composition comprising a sulfonyl amide salt represented by the formula:

$$(R^2SO_2NM_b)_{3-b}M'_c \quad \text{(III)}$$

wherein $R^2$ is aryl, fluoro-aryl, or $XCF_2$— where X is H, halogen, fluorinated or non-fluorinated linear or cyclic alkyl radicals having 1–10 carbons, optionally substituted by one or more ether oxygens, M' is an alkaline earth metal, b=1 or 2, c=0 or 1, M is an alkaline earth when b is 1 or an alkali metal when b is 2 and c=0, and M is alkali metal when b=1 and c=1, with the proviso that c is not equal to 1 when b=2 with a non-polymeric sulfonyl fluoride composition represented by the formula $R^1(SO_2F)_m$ (IV)

wherein m=1 or 2, where, when m=1, $R^1$ is a fluorinated or non-fluorinated, saturated or unsaturated hydrocarbyl radical, except perfluoroolefin, having 1–12 carbons optionally substituted by one or more ether oxygens, or tertiary amino; or, when m=2, $R^1$ is a fluorinated or non-fluorinated, saturated or unsaturated hydrocarbylene, except perfluoroalylene, radical having 1–12 carbons optionally substituted by one or more ether oxygens;

or with a polymeric sulfonyl fluoride composition comprising monomer units represented by the formula $$-[CZ_2CZ(R^3SO_2F)]- \quad \text{(V)}$$

wherein $R^3$ is a diradical selected from the group consisting of fluorinated or non-fluorinated allylene, including oxyalkylene or fluorooxyalkylene, but not perfluoroalkylene, and each Z is independently hydrogen or halogen, and the Zs need not be the same; and, causing them to react to form a non-polymeric imide composition represented by the formula:

$$\{R^1[SO_2NSO_2R^2]_m\}_y \quad \text{(I)}$$
$$\mid$$
$$M$$

wherein y=1 or 2, M is an alkali when y is 1 or an alkaline earth metal when y is 2, m=1 or 2, where, when m=1, $R^1$ is a fluorinated or non-fluorinated, saturated or unsaturated hydrocarbyl radical, except perfluoroolefin, having 1–12 carbons optionally substituted by one or more ether oxygens, or tertiary amino; or, where m=2, $R^1$ is a fluorinated or non-fluorinated, saturated or unsaturated hydrocarbylene, except perfluoroalkylene, radical having 1–12 carbons optionally substituted by one or more ether oxygens, with the proviso that when y=2 and m=2, M may represent a combination of alkali and alkaline earth metals;

or, in the alternative, a polymeric imide composition comprising monomer units represented by the formula:

(II)

wherein y=1 or 2; $R^3$ is a diradical selected from the group consisting of fluorinated or non-fluorinated alkylene, including oxyalkylene or fluorooxyalkylene, each Z is independently hydrogen or halogen, wherein the Z's need not be the same; $R^2$ is aryl, fluoro-aryl, or $XCF_2$— where X is H, halogen, fluorinated or non-fluorinated linear or cyclic alkyl radicals having 1–10 carbons, optionally substituted by one or more ether oxygens; M is an alkali when y is 1 or an alkaline earth metal when y is 2.

As used herein, the term "reacting" is intended to mean allowing or to allow at least two components in a reaction mixture to react to form at least one product. "Reacting" may optionally include stirring and/or heating or cooling.

DETAILED DESCRIPTION

The process of the present invention represents a simple method of providing a very wide range of imides which can be readily and variously ion exchanged to provide superacid catalysts, electrolytes, and ionomers useful for electrochemical applications.

In the practice of the invention it is not necessary to first protect the double bond of an olefinic or vinyl ether prior to imidization. The imidization will proceed without attacking the double bond.

Equally useful is the imidizationdblhapolymer comprising monomer units of vinylidene fluoride and monomer units comprising a pendant group having sulfonyl fluoride functionality, particularly a perfluorovinyl ether perfluoroalkoxysulfonyl fluoride, such as described in Doyle et al., WO 9941292(A1). The methods of the art for converting sulfonyl fluorides to imides are not applicable to the copolymers of WO 9941292(A1) and others embodiments containing vinylidene fluoride monomer units because of the base instability of the vinylidene fluoride moiety. Application of the methods of the art result in extensive and unacceptable degradation of the polymer backbone in vinylidene fluoride containing polymers. The method of the present invention provides for conversion of sulfonyl fluoride to imide in vinylidene fluoride containing polymers without degradation of the polymer backbone.

In the present invention, the term "hydrocarbyl" is employed to mean a monoradical consisting of carbon and hydrogen. Included in the term "hydrocarbyl" are alkyl, cycloalkyl, aryl, aryl alkyl and the like. Similarly, the term "hydrocarbylene" is employed to mean a diradical consisting of carbon and hydrogen. Both hydrocarbyl and hydrocarbylene radicals, as employed herein, may contain one or more unsaturated carbon-carbon bonds, one or more ether oxygens, and may be partially or fully fluorinated. Essentially any hydrocarbyl or hydrocarbylene radical is suitable for the practice of the invention except that radicals containing perfluoroolefin functionality are not suitable for the practice of the invention. Perfluorovinyl ether functionality however is preferred. Thus, the functional group $CF_2=CF-CF_2-$ is not suitable but the functional group $CF_2=CF-O-$ is not only suitable but is also preferred.

In one aspect of the present invention, dimetal sulfonyl amide salts having the formula $(R^2SO_2NM_b)_{3-b}M'_c$ (III) are found to be highly effective agents for preparing imides from a wide variety of compounds having a sulfonyl fluoride functionality, both from polymeric and non-polymeric species. In the dimetal sulfonyl amide salts suitable for the process of the invention, $R^2$ is aryl, fluoro-aryl, or $XCF_2$— where X is H, halogen, fluorinated or non-fluorinated linear or cyclic alkyl radicals having 1–10 carbons, optionally substituted by one or more ether oxygens, M' is an alkaline earth metal, b=1 or 2, c=0 or 1, M is an alkaline earth when b is 1 or an alkali metal when b is 2 and c=0, and M is alkai metal when b=1 and c=1, with the proviso that c is unequal to 1 when b=2.

Preferably, $R^2$ is fluoroalkyl having 1–4 carbons; most preferably $R^2$ is $CF_3$—. Preferably, M is an alkali metal, most preferably sodium, and b=2.

In one embodiment, a non-polymeric sulfonyl fluoride composition represented by the formula $R^1(SO_2F)_m$ in liquid dispersion or solution is contacted with the dimetal sulfonyl amide salt(III) to form a reaction mixture. m=1 or 2, where, when m=1, $R^1$ is a fluorinated or non-fluorinated, saturated or unsaturated hydrocarbyl radical having 1–12 carbons optionally substituted by one or more ether oxygens, except perfluoroolefin, or tertiary amino; or, when m=2, $R^1$ is a fluorinated or non-fluorinated, saturated or unsaturated hydrocarbylene, except perfluoroalkylene, radical having 1–12 carbons optionally substituted by one or more ether oxygens, preferably m=1. More preferably m=1, $R^1$ is a perfluorovinyl ether represented by the formula:

wherein $R^4$ is F or perfluoroalkyl having 1–4 carbons, z=0 or 1, and n=0–3. Most preferably m=1 and $R^4$ is trifluoromethyl, z=1, and n=0 or 1.

In one embodiment, the process of the invention may be conducted in the absence of an inert liquid diluent when a sufficient excess of a liquid $R^1(SO_2F)_m$ is provided to ensure good mixing. However, in the absence of an inert diluent, the reaction may proceed inhomogeneously, and is potentially subject to sudden decomposition. Therefore, it is preferred to conduct the process of the invention in an inert liquid diluent. Numerous aprotic organic liquids are suitable for use as an inert liquid diluent for the process of the invention; the requirements are not strict beyond liquidity and inertness. It is preferred to use a solvent that dissolves the monomer but not the NaF by-product so that it can easily be filtered off. Preferred liquids are ethers, including THF, nitrites, DMSO, amides, and sulfolanes. Ethers are more preferred, with THF most preferred.

The reaction may be conducted at any temperature between the freezing and boiling point of the inert liquid diluent. Room temperature has been found to be satisfactory in the preferred embodiment of the invention. Temperatures from room temperature to 80° C. are suitable, with room temperature to 60° C. more preferred.

The reaction mixture is preferably stirred or otherwise agitated according to means commonly employed in the art.

In a first preferred embodiment of the process of the invention, the product of the process is most preferably as represented by the formula:

$$CF_2=CFO-[CF_2CF(CF_3)-O]_n-CF_2CF_2SO_2N(Na)SO_2CF_3 \quad (VIII)$$

where n=0 or 1. It is a particularly surprising aspect of the present invention that the conversion of the —SO₂F group may be effected without the necessity of protecting the double bond. The product so-formed, (VIII), may advantageously be employed as a comonomer with fluorinated olefins, non-fluorinated olefins, fluorinated vinyl ethers, non-fluorinated vinyl ethers, and combinations thereof. Preferred comonomers include ethylene, tetrafluoroethylene, hexafluoro-propylene, perfluoroalkyl vinyl ether, vinylidene fluoride, and vinyl fluoride. Copolymerizing the monomer (VIII) with a variety of co-monomers may be effected for example according to the teachings of DesMarteau, op.cit. or of Feiring et al., op.cit. or, more broadly, may be effected according the methods of Connolly et al., op. cit. The ionomers so formed are useful in a wide variety of electrochemical applications.

One area of particular utility is in lithium batteries. For this purpose, the product monomer, (VIII), may be ion exchanged to the lithium form by contacting the monomer (VIII) with a dilute solution of LiCl in THF. The polymerizations indicated above may then be effected. In the alternative, the polymerizations may first be effected, followed by ion exchange with LiCl in THF. In an alternative embodiment, the preferred sodium imide of the invention can be treated with aqueous acid to form the acid followed by treatment with aqueous lithium salt to form the lithium ion composition.

In a further embodiment a sulfonyl fluoride polymer composition is contacted with the dimetal sulfonyl amide salt (III) in liquid dispersion or solution to form a reaction mixture. The polymer comprises monomer units represented by the formula $$-[CZ_2CZ(R^3SO_2F)]- \quad (V)$$

wherein $R^3$ is a diradical selected from the group consisting of fluorinated or non-fluorinated alkylene, but not perfluoroalkylene, including oxyalkylene or fluorooxyalkylene, and each Z is independently hydrogen or halogen, and need not be the same. Preferably, $R^3$ is oxyalkylene. In a second preferred embodiment (V) is represented by the formula:

$$-CF_2-CF-\\ \quad\quad |\\ \quad\quad O-[CF_2CF(R^4)-O_z]_a-CF_2CF_2SO_2F \quad (IX)$$

wherein $R^4$ is F or perfluoroalkyl having 1–4 carbons, z=0 or 1, and a=0–3. Most preferably $R^4$ is trifluoromethyl, z=1, and a=0 or 1.

The polymer comprising the moor units (IX) may comprise up to 50 mol % of said monomer units (IX). Comonomer units incorporated therewith may be derived from numerous olefinically unsaturated species as identified in the art including, ethylene, vinylidene fluoride (VF₂) vinyl fluoride, and combinations thereof to form terpolymers. Additional termonomers include tetrafluoroethylene, hexafluoropropylene, perfluoroalkyl vinyl ethers, and such other ethylenically unsaturated species as are known in the art.

Particularly preferred for the practice of the invention is a copolymer comprising up to 50 mol %, most preferably up to 20 mol %, of comonomer units (IX) and comonomer units derived from VF₂, most preferably at least 50 mol % of monomer units derived from VF₂. It is a surprising aspect of the present invention that the copolymer of (IX) with at least 50 mol % of units derived from VF₂ can be successfully reacted according to the process of the invention to form the corresponding imide. Because of the well-known base instability of VF₂-containing polymers, the methods of the art for forming imides from sulfonyl fluorides are not operable with polymers having any more than trace amounts of monomer units derived from VF₂ because the imidizing agents of the art attack the polymer backbone causing extensive degradation.

There is no particular limitation on the molecular weight of polymers suitable for the practice of the invention. Oligomeric polymers may themselves be liquids at or near room temperature and therefore are well-suited as the liquid dispersing medium of the process. However, it is generally preferred to employ an inert diluent, preferably a solvent for the polymer. As the molecular weight of the polymer increases, solubility and solution viscosity become increasingly difficult problems, making homogeneous reaction difficult. The preferred copolymer of VF₂ and comonomer (IX) is particularly well-suited to the practice of the present invention because of the relatively higher solubility of VF₂-containing polymers in non-fluorinated solvents than other fluoropolymers.

Numerous aprotic organic liquids are suitable for use as solvents for the sulfonyl fluoride polymer composition in the process of the invention. As stated, solubility of the polymer reactant is a limiting factor. Preferred solvents are ethers, including THF, nitriles, DMSO, amides, and sulfolanes. Ethers are more preferred, with THF most preferred. Because of the limitations on solubility associated with high molecular weight, lower molecular weight polymers are preferred.

Suitable and preferred reaction temperatures are as in the case of the non-polymeric reactant hereinabove described.

For the purposes herein, the polymer produced in the process of the invention is represented by the formula:

$$\{-[CZ_2CZ(R^3SO_2NSO_2R^2)]-\}_y\\ \quad\quad\quad\quad\quad\quad |\\ \quad\quad\quad\quad\quad\quad M$$

wherein y=1 or 2; $R^3$ is a diradical selected from the group consisting of fluorinated or non-fluorinated alkylene, including oxyalkylene or fluorooxyalkylene, each Z is independently hydrogen or halogen, wherein the Zs need not be the same; $R^2$ is aryl, fluoro-aryl, or $XCF_2$— where X is H, halogen, fluorinated or non-fluorinated linear or cyclic alkyl radicals having 1–10 carbons, optionally substituted by one or more ether oxygens; M is an alkali when y=1 or an alkaline earth metal when y=2. When y=2, M is an alkaline earth metal. Setting y=2 is meant to designate that the alkaline earth metal, M in (II), which has a valence of 2, is bonded to two different polymer chains each of the indicated composition, thus serving as a metallic cross-link. It is also possible, depending upon chain configuration, for the alkaline earth metal M to be bonded to two segments of the same polymer chain.

The process of the present invention is preferably practiced with a purified form of the dimetal sulfonyl amide salt (D). Xue, op.cit., teaches only a process which provides very small amounts of highly contaminated (II). The inventors of the present invention have determined by ordinary methods of chemical analysis that Xue's process produced $CF_3SO_2NNa_2$ with conversion of less than 10%, most of the remainder of his reaction product being unconverted starting material. No method is provided in the art for preparing (III) in pure form.

In the process of the invention, the dimetal sulfonyl amide salt starting material $(R^2SO_2NM_b)_{3-b}M'_c$, (III), should first itself be produced at high yield. In (III), $R^2$ is aryl, fluoro-aryl, or $XCF_2$— where X is H, halogen, fluorinated or non-fluorinated linear or cyclic alkyl radicals having 1–10 carbons, optionally substituted by one or more ether oxygens, M' is an alkaline earth metal, b=1 or 2, c=0 or 1, M is an alkaline earth when b=1 or an alkali metal when b=2 and c=0, and M is alkali metal when b=1 and c=1, with the proviso that c is not equal to 1 when b=2.

Preferably, M is an alkali metal and c=0, b=2, and $R^2$ is a perfluoroalkyl radical. Most preferably M is sodium and $R^2$ is a trifluoromethyl radical. The inventor hereof has found that surprisingly dimetal sulfonyl amide salt (III) can be made at much higher purities than in Xue's process, purity of greater than 50%, preferably greater than 90%, most preferably greater than 95%, by contacting a sulfonyl amide or monometal sulfonyl amide salt thereof having the formula $(R^2SO_2NH)_{3-a}M''$, (VII), with at least one alkali or alkaline earth metal hydride and an aprotic liquid to form a reaction mixture which is permitted to react to any desired degree of conversion up to 100%, which is preferred. In the sulfonyl amide or monometal salt thereof (VII), a=1 or 2, M'' is alkaline earth metal when a=1, M'' is alkali metal or hydrogen when a=2, and $R^2$ is aryl, fluoro-aryl, or $XCF_2$— where X is H, halogen, or a fluorinated or non-fluorinated linear or cyclic alkyl radical having 1–10 carbons, optionally substituted by one or more ether oxygens. In the hydride may be a mixture of more than one alkali or alkaline earth hydrides, or a mixture of alkali and alkaline earth hydrides. If preferred, the reaction may proceed in stages with different hydrides being fed to the reaction at different times.

Preferably $R^2$ is perfluoroalkyl, most preferably trifluoromethyl, and M'' is sodium. $CF_3SO_2NH_2$ is the preferred starting material for preparing the $CF_3SO_2NNa_2$ preferred for the process of the present invention. The preferred aprotic liquid is acetonitrile. Preferably the reaction to produce the $CF_3SO_2NNa_2$ is continued until one or the other starting material is completely consumed and reaction stops. More preferably the stoichiometry is adjusted so that only trace amounts of either starting material remain when reaction is complete. Most preferably, the hydride is added at slightly below stoichiometric quantity.

The sulfonyl amide and monometal salt thereof (VII) are soluble in the aprotic solvents employed in the process of preparing the dimetal sulfonyl amide salt (III), but the dimetal sulfonyl amide salt (III) itself is not. The solubility difference is exploited herein to separate the reaction product from the reaction mixture and obtain a composition comprising sulfonyl amide salts at least 50 mol %, preferably at least 90 mol %, most preferably at least 95 mol %, of which salts are represented by the formula $(R^2SO_2NM_b)_{3-b}M_c'$, (III), as hereinabove defined. Any convenient method known in the art for separating solids from liquids may be employed, including filtration, centrifugation and, distillation.

While it is preferred to permit the synthesis of (III) to run to completion, this may not always be practical depending upon the aprotic solvent chosen. In neat acetonitrile, 100% conversion is achieved in ca. 4 hours at room temperature. However, in neat THF, six days of reaction are required for 100% conversion. In the latter case, it may be desired to separate the reaction product before the reactants have fully reacted. The method of separation based upon the heretofore unknown solubility difference hereinabove described provides a practical method for isolating the dimetal sulfonyl amide salt (III) at high purity when conversion has been low.

It has been found in the practice of the present invention that residual hydride left over from the synthesis of the dimetal sulfonyl amide salt (III) is not highly deleterious to the efficacy of the process of the present invention. While not critical, the $CF_3SO_2NNa_2$ preferred for the process of the present invention is substantially free of contamination by NaH. This is achieved by employing slightly less than the stoichiometric amount of NaH in its preparation, thereby insuring that when the reaction achieves full conversion, the NaH will be exhausted. Any excess of the soluble intermediate $CF_3SO_2NHNa$ is easily separated by washing/filtration cycles, preferably using fresh aliquots of solvent.

In preparing the dimetal sulfonyl amide salt, (III) it has been found that the components of the reaction mixture may be combined in any order, but that it is preferred to first mix the sulfonyl amide or a monometal salt thereof (II), with the aprotic liquid to form a solution, following with addition of the hydride after the solution has formed. First mixing the hydride with the aprotic solvent has resulted in poor reaction or slower than expected conversion.

A suitable temperature for preparing the dimetal sulfonyl amide salt (III) will lie between the melting point and the boiling point of the aprotic liquid selected. It has been found to be satisfactory for the practice of the invention to conduct the process of the invention at room temperature. However, somewhat higher temperatures result in faster reaction. In the most preferred embodiment of the invention, acetonitrile is employed as the solvent at a temperature between 0° C. and 80° C., preferably between room temperature and 80° C., most preferably between room temperature and 60° C.

Aprotic solvents suitable for preparing the dimetal sulfonyl amide salt (III) should be substantially free of water. Water causes the reaction to go in the wrong direction, for example to form $CF_3SO_2NHNa$ and NaOH, and provides a route for making a sulfonate instead of an imide. In a preferred embodiment, it has been found satisfactory to employ acetonitrile having water content less than or equal to ca 500 ppm, with water content less than or equal to ca. 50 ppm more preferred. Acetonitrile is quite hygroscopic, and care should be taken in handling to avoid water contamination from the atmosphere.

The preferred aprotic solvent for the preparation of the dimetal sulfonyl amide salt (III) comprises acetonitrile. Acetonitrile has been found to accelerate the conversion by a considerable amount over other aprotic solvents. In neat acetonitrile, essentially quantitative conversion is achieved in ca. 4 hours. In the presence of as little as 5% acetonitrile in the THF taught by Xue,op. cit., essentially quantitative conversion is achieved in ca. 25 h. These results contrast starkly with the six days required under the conditions taught by Xue.

It is found that solvent selection has a tremendous effect on the rate of conversion, though most aprotic solvents will lead to high conversion over sufficient time. Acetonitrile is highly preferred. Other aliphatic and aromatic nitrites, while suitable, do not appear to be particularly better than the THF employed by Xue but may be employed as substitutes for THF. Suitable nitrites include higher alkyl nitrites, dinitriles such as adiponitrile, benzonitrile, and the like. Other suitable solvents include ethers, DMF, DMSO, DMAC, and amides. Combinations of suitable solvents are also suitable.

Any of the methods hereinabove, alone or in combination, provide a highly purified form of the sufonyl amide salt (III)

in dramatic distinction over the practice of Xue. The highly purified form of $(R^2SO_2NM_b)_{3-b}M'$, (III), greater than 95% purity, which is readily achieved using the methods herein described, is then suitable for use in the process of the present invention producing pure imides, (I) or (II), at high yields, the purity thereof depending directly upon the purity of (III). Any of the methods of preparation herein described are capable of providing (III) in purities of greater than 95%.

The atmosphere to which the dimetal sulfonyl amide salt (III) is exposed should be substantially free of water as well. Water vapor concentrations of about 25 ppm have been found to be highly suitable. Higher levels of water vapor concentration can be tolerated, but it should be understood that the higher the water vapor concentration of the atmosphere, the greater the contamination during subsequent reaction. As a general rule, the less water, the better, in whatever form.

The term "inert atmosphere" as used herein refers to an anhydrous atmosphere having a water vapor concentration of less than ca. 50 ppm. It is not meant to imply a non-oxidative atmosphere. Thus, the reactions herein may be accomplished in desiccated air as well as in dry nitrogen or other non-chemically active gases. Dry nitrogen, however, is preferred.

In a preferred method of preparation of the dimetal sulfonyl amide salt (III), $CF_3SO_2NH_2$ is dissolved at a concentration in the range of 5–10% by weight in acetonitrile in an inert atmosphere such as nitrogen. At higher concentrations good mixing may become more difficult to maintain as the insoluble $CF_3SO_2NNa_2$ product begins to form, creating a dispersion. Therefore at concentrations higher than about 10% by weight, other forms of agitation may be preferred over simple stirring, such as ultrasonic agitation, or microfluidization such as may be achieved using a MicroFluidizer™ available from Microfluidics, Inc., Newton, Mass.

While maintaining the inert atmosphere, NaH is added with agitation continued until the reaction is complete in about 4 hours. Hydrogen gas evolution rate, determined by any convenient method known in the art, has been found to be an effective indicator of reaction. The cessation of hydrogen gas flow signals completion of the reaction.

The amount of NaH added depends upon the particular requirements and intentions of the practitioner hereof. Adding a slight excess over the stoichiometric amount of NaH ensures complete conversion of the $CF_3SO_2NH_2$ or $CF_3SO_2NHNa$ to $CF_3SO_2NNa_2$. However, this leaves $CF_3SO_2NNa_2$ so prepared still contaminated with insoluble NaH from which it is difficult to separate. However, it has been found that residual NaH is largely inert in the process of the invention and to the products thereof. On the other hand, if the goal is to achieve the cleanest possible $CF_3SO_2NNa_2$ then a slight deficit of NaH below the stoichiometric amount may be employed to ensure that the NaH will be fully consumed. Employing a deficit of NaH will result in less than complete conversion of the $CF_3SO_2NH_2$ or $CF_3SO_2NHNa$ to $CF_3SO_2NNa_2$. The soluble residual intermediary $CF_3SO_2NHNa$ is easily washed away from the insoluble $CF_3SO_2NNa_2$.

The dimetal sulfonyl amide salt (III) may be dried under vacuum at elevated temperature but the user must be aware of the possibility of spontaneous and violent decomposition of the material. It is highly recommended to never handle this material in a totally dry state. It is highly recommended to keep the material wet at all times. It seems that the smaller composition $CF_3SO_2NNa_2$ is less stable than the compositions of higher molecular weight like $C_4F_9SO_2NNa_2$. A suitable temperature depends upon the specific composition thereof. The preferred $CF_3SO_2NNa_2$ should be dried at a temperature preferably not higher than 80° C., most preferably not higher than 65° C. Certain of the compositions of the invention, including the preferred $CF_3SO_2NNa_2$, have been observed to undergo certain decomposition aggressively when heated to the decomposition threshold but it has also been observed at one occasion that the preferred $CF_3SO_2NNa_2$ undergoes spontaneous decomposition at room temperature. The compound is moisture sensitive and should be handled under anhydrous conditions. It is believed that the product is somewhat unstable, and potentially may be subject to explosive decomposition.

EXAMPLES

Example 1

$CF_3SO_2NH_2$ was purchased from Tokyo Chemical Industry, Portland, Oreg., (TCI) and dried and purified by two cycles of sublimation under a vacuum of about (0.1 Pa, $10^{-3}$ Torr), employing a water cooled (~20° C.) cold-finger, and an oil bath at 80° C. Anhydrous acetonitrile was purchased from EM Science Gibbstown, N.J., slurried with $P_2O_5$ and distilled to ensure dryness, and stored over molecular sieves inside a dry box until ready to be used. Sodium hydride (95%) was purchased from Aldrich Chemical.

Inside a model HE-63-P dry-box (Vacuum Atmosphere Company, Hawthorne, Calif.) having a dry nitrogen atmosphere, a round bottom flask was charged with 30.003 g of the sublimed $CF_3SO_2NH_2$ and 750 ml of the dried acetonitrile. 9.003 g of the sodium hydride was slowly added over a period of 60 min while the reaction mixture was stirred with a magnetic stir bar. The temperature of the reaction mixture increased from 21.6° C. to 50.5° C. during the addition process. The mixture was stirred at room temperature for 20 h. After about 4–5 hours the reaction medium had taken on an opaque "creamy" appearance, and no further bubbling, indicative of the evolution of hydrogen, was observed.

The reacted mixture was filtered through a glass-filter (medium porosity) inside the dry-box. The white solid was washed three times with 100 ml of the anhydrous acetonitrile, transferred from the filter to a Schlenk flask and dried under vacuum (1 Pa, $10^{-2}$ Torr) at room temperature for 5 h, still in the dry box. Approximately 10% of the filtrate was lost in transferring from the filter to the Schlenk flask. The Schlenk flask was sealed, removed from the dry-box, and subject to further evacuation under oil pump vacuum (0.1 Pa, $10^{-3}$ Torr) for 15 h at room temperature. The Schlenk flask was then immersed in an oil bath set at 50° C. and held for four hours at which time the bath was heated to 65° C. and the 20 Schlenk flask was held therein for an additional 20 h while still subject to evacuation under oil pump vacuum (0.1 Pa, $10^{-3}$ Torr). Afterwards, the $CF_3SO_2NNa_2$ was only handled inside the dry-box.

30.0 grams of product were isolated. The product decomposed at 110° C. while generating large amounts of a gas.

It has been observed at one occasion that the preferred $CF_3SO_2NNa_2$ undergoes spontaneous decomposition at room temperature and it is therefore recommended to not dry this material but instead keep it as a suspension at all times.

Example 2

Inside the dry box of Example 1, a flask was charged with 5.142 g $C_4F_9SO_2NH_2$ made from $C_4F_9SO_2F$ and $NH_3$ according to the method of MeuBdoerffer et al, op. cit., and 100 ml of anhydrous acetonitrile prepared as in Example 1. 0.784 g NaH (Aldrich) was slowly added over a period of 5 min. The mixture was stirred at room temperature for 24 h without observation. Insoluble $C_4F_9SO_2NNa_2$ had precipitated at the bottom of the flask. The reaction mixture was filtered through a glass filter (fine porosity) and the white residue was washed three times with 50 ml of anhydrous acetonitrile. The residue was collected from the filter and placed in a Schlenk-flask. Afterwards, the material was brought outside the dry-box and dried under oil pump vacuum (0.1 Pa, $10^{-3}$ Torr) for 24 h at an oil bath temperature of 65° C. $C_4F_9SO_2NNa_2$ was only handled inside the dry-box. 4.37 g of product were isolated.

It has been observed at one occasion that the preferred $CF_3SO_2NNa_2$ undergoes spontaneous decomposition at room temperature and it is therefore recommended to not dry this material but instead keep it as a suspension at all times.

Example 3

Employing the reagents and equipment of Example 1, inside the dry-box 3.123 g of the sublimed $CF_3SO_2NH_2$ was dissolved in 100 ml of the anhydrous acetonitrile in a round-bottom flask. 1.127 g of the sodium hydride was slowly added to form a first reaction mixture. Addition of NaH took place over a period of 10min while the first reaction mixture was stirred with a magnetic stirring bar at room temperature. After 3 h, no fluorine could be detected by $^{19}F$ NMR in the solution indicating complete conversion of $CF_3SO_2NH_2$ to $CF_3SO_2NNa_2$, thereby forming a mixture of $CF_3SO_2NNa_2$ and acetonitrile, with some residual NaH.

$CF_2$=$CFOCF_2CF(CF_3)OCF_2CF_2SO_2F$ (PSEPVE) prepared according to the method of Connolly et al., U.S. Pat. No. 3,282,875, was slurried with $P_2O_5$ and distilled. 10.002 g of the thus-treated PSEPVE was added to the mixture of $CF_3SO_2NNa_2$ and acetonitrile prepared as hereinabove to form a second reaction mixture. The second reaction mixture was stirred at room temperature. After 10 min, the mixture turned clear, indicative of complete reaction of the $CF_3SO_2NNa_2$, and then slightly cloudy, indicative of the precipitation of the NaF by-product After 30 minutes fluorine NMR confirmed a substantial concentration of the imidized form of PSEPVE. The reacted mixture was centrifuged and then filtered through a glass filter (medium porosity). The residue was washed with 100 ml of anhydrous acetonitrile. All volatiles were removed under vacuum of 0.1 Pa, $10^{-3}$ Torr at room temperature and the slightly beige residue was heated to 110° C. for 16 h at 0.1 Pa, $10^{-3}$ Torr. Yield was 9.494 g.

$^{19}F$ NMR in $CD_3CN$ confirmed the structure $CF_2$=$CFOCF_2CF(CF_3)OCF_2CF_2SO_2N(Na)SO_2CF_3$.

$^{19}F$ NMR in $CD_3CN$/Freon-11

($CF_2^{A,A'}$=$CF^BOCF_2^CCF^D(CF_3^E)OCF_2^FCF_2^GSO_2N(Na)$
$SO_2CF_3^H$): −112.6, −120.9 ppm (A, 1F, A', 1F), −135.7 ppm (B, 1F), −78.0 ppm ($CF_2$, C, 2F), −144.2 ppm (CF, D, 1F), −79.1 ppm ($CF_3$, E, 3F), −83.7 ppm ($CF_2$, F, 2F), −116.0 ppm ($CF_2$, G, 2F), −78.9 ppm ($CF_3$, H, 3F). MS: Negative electron spray; 574.14, M-Na.

Example 4

Inside the dry-box of Example 1, a round bottom flask was charged with 5.027 g of the $C_4F_9SO_2NH_2$ made from $C_4F_9SO_2F$ and $NH_3$ according to the method of MeuBdoerffer et al, op.cit., and 100 ml of anhydrous acetonitrile prepared as in Example 1. 0.890 g of sodium hydride (Aldrich) was slowly added to form a first reaction mixture. Addition of NaH took place over a period of 10 min while the reaction mixture was stirred at room temperature with a magnetic stir bar. After 22 h of siring, no fluorine could be detected by $^{19}F$ NMR in the solution indicating complete conversion, thereby forming a mixture of $C_4F_9SO_2NNa_2$ in acetonitrile, contaminated by some residual NaH.

7.797 g of the PSEPVE of Example 3 was added to the mixture of $C_4F_9SO_2NNa_2$ and acetonitrile prepared hereinabove to form a second reaction mixture. The second reaction mixture was stirred at room temperature. After 10 min, the mixture turned clear, indicative of complete reaction of the $CF_3SO_2NNa_2$, and then slightly cloudy, indicating the precipitation of the NaF by-product. NMR of the reaction mixture taken after 30 min confirmed the substantial presence of the imidized form of PSEPVE. The reaction mixture was centrifuged and then filtered through a glass filter (medium porosity). The residue was washed with 100 ml of anhydrous acetonitrile. All volatiles were removed under vacuum and the slightly beige residue was heated to 110° C. for 16 h at 1 Pa, $10^{-3}$ Torr. Yield was 8.358 g.

$^{19}F$ NMR in $CD_3CN$ confirmed the structure $CF_2$=$CFOCF_2CF(CF_3)OCF_2CF_2SO_2N(Na)SO_2(CF_2)_3CF_3$ $^{19}F$ NMR in $CD_3CN$/Freon-11

($CF_2^{A,A'}$=$CF^BOCF_2^CCF^D(CF_3^E)OCF_2^FCF_2^GSO_2N(Na)SO_2CF_2^HCF_2^ICF_2^JCF_3^K$): −112.6, −120.7 ppm (A, 1F, A', 1F), −135.6 ppm (B, 1F), −78.0 ppm ($CF_2$, C, 2F), −144.1 ppm (CF, D, 1F), −79.1 ppm ($CF_3$, E, 3F), −83.7 ppm ($CF_2$, F, 2F), −115.9 ppm ($CF_2$, G, 2F), −112.6 ppm ($CF_2$, H, 2F), −120.6 ppm ($CF_2$, I, 2F), −125.8 ppm ($CF_2$, J, 2F), −79.1 ppm ($CF_3$, K, 3F).
MS: Negative electron spray; 723.98, M-Na.

Example 5

Benzonitrile (Aldrich)was dried by mixing with $P_2O_5$ and then distilling. Employing reagents and equipment of Example 1, inside the dry-box 3.008 g of the sublimed $CF_3SO_2NH_2$ was dissolved in 90 ml of the dried benzonitrile in a round-bottom flask To form a first reaction mixture, 1.018 g of the sodium hydride was slowly added while the reaction mixture was stirred with a magnetic stirring bar at room temperature. The reaction mixture changed its appearance after 10 min. A white precipitate was formed causing a thickening of the slurry. Shortly after, the reaction mixture changed its color to yellow. After 60 min, the reaction mixture was red. After 6 h, fluorine could still be detected by $^{19}F$ NMR in the solution. After a total of 24 h at room temperature, 8.511 g of PSEPVE of Example 3 was added, thereby forming a second reactions mixture. The second reaction mixture was stirred at room temperature. The color changed from red to yellow. $^{19}F$ NMR in $CD_3CN$ after 2 h confirmed the formation of the structure $CF_2$=$CFOCF_2CF(CF_3)OCF_2CF_2SO_2N(Na)SO_2CF_3$.

Example 6

Figure 1:
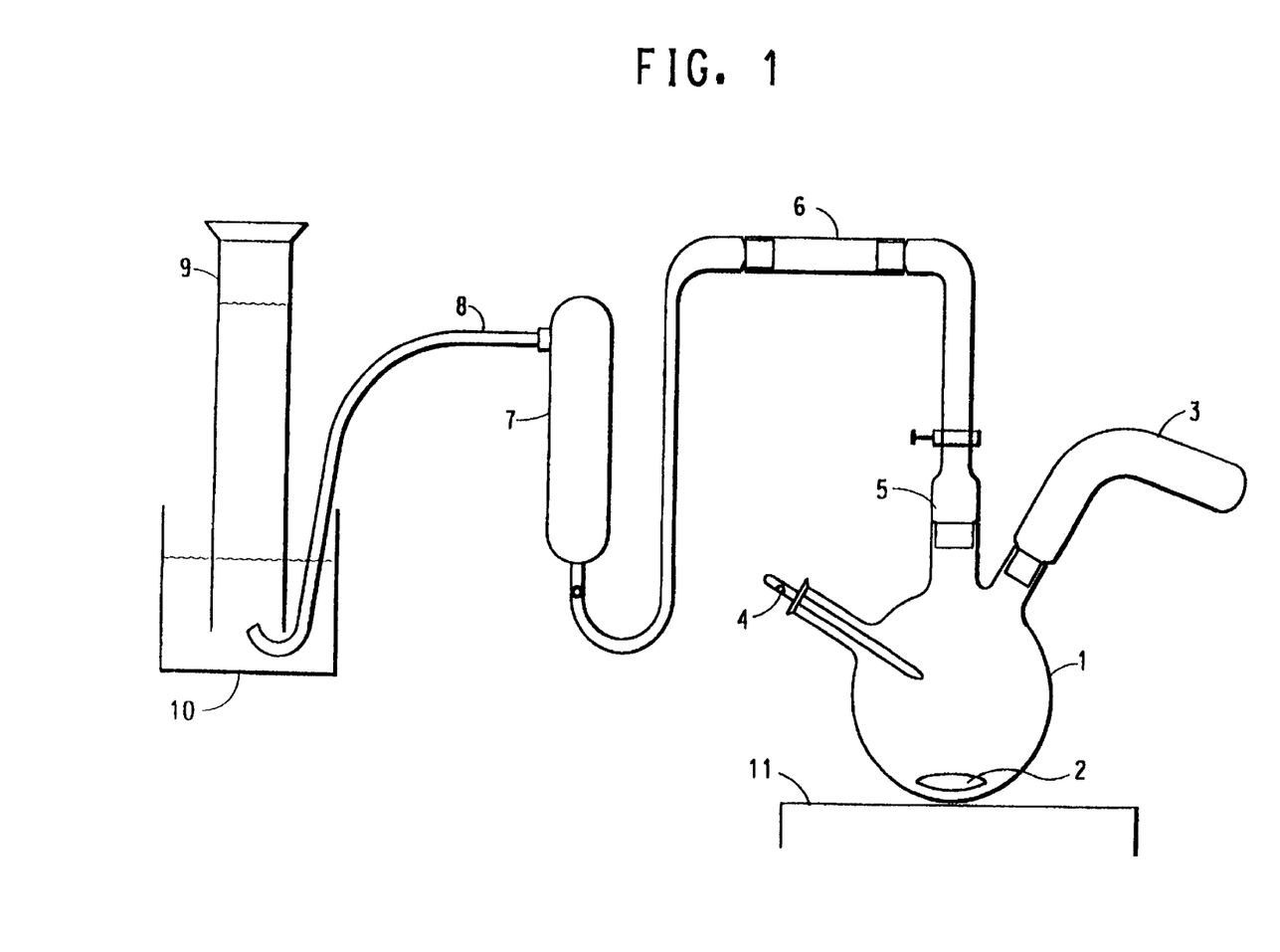
FIG. 1 is a representation of the apparatus employed for determining the volume of hydrogen gas evolved from the reactions described in the specific embodiments herein.

In this Example, an apparatus was employed for determining the volume of hydrogen gas evolved by the reaction as a function of time. The apparatus is depicted in FIG. 1. One neck of a three necked round bottom flask, 1, holding a magnetic stirring bar, 2, was fitted with a solid reactant addition device SRAD, 3, having a 75° angle to be employed for feeding a solid to the flask. A second neck was fitted with a thermocouple probe, 4, and a third neck was fitted with a stopcock, 5. The stopcock, 5, was connected via a 4 cm piece of Tygon® tubing, 6, to an Aldrich Safe-purge (TM) valve, 7, containing mineral oil. The Safe-purge valve, 7, was connected via a rubber hose, 8, to a water-filled 250 ml graduated cylinder, 9, that is deployed upside-down in a water-filled 600 ml beaker, 10. In operation liquid reactants were charged to the flask through any of the necks, SRAD, 3, was charged with the desired amount of solid reactant and reaffixed to the flask, 1, in the downward-pointing position shown in the figure. The beaker, 10, was filled to about 50% of capacity with water while the graduated cylinder, 9, was filled completely with water. The stopcock, 5, was opened, and the adaptor, 3, was inverted thus delivering the solid reactant to the reactants in the flask and thereby initiating the reaction. As hydrogen was evolved from the reaction it displaces the water from the graduated cylinder providing a volumetric means for determining the rate and total amount of hydrogen evolution.

Employing the methods and material of Example 1, inside the dry-box, 0.546 g of the sublimed $CF_3SO_2NH_2$ was dissolved in 100 ml of the anhydrous acetonitrile in the three neck round bottom flask of FIG. 1. 0.213 g of the sodium hydride was carefully placed in the SRAD. The flask was carefully brought outside the dry box and connected to the remainder of the apparatus of FIG. 1. After all connections had been established, the stopcock to the reaction flask was opened. The reaction mixture was stirred at room temperature and the SRAD was inverted thereby feeding the NaH to the solution in the flask. Immediately, a reaction could be observed. 80 ml of gas were collected over a period of 5 min. The temperature of the reaction mixture increased from 23° C. to 26° C. Over the next 120 min, the formation of gas slowed down and 74 ml of gas were collected in the graduated cylinder. During this period, the appearance of the reaction mixture changed. The fine residue in the reaction mixture changed to a thicker precipitate that settled easily to the bottom of the flask when the stirring was stopped. The reaction mixture was stirred for another hour at room temperature, 10 ml of additional gas were collected during this period. The flask was brought into the dry box and a sample of the solution was submitted for NMR. No fluorine could be detected, indicating the complete conversion of $CF_3SO_2NHNa$ into insoluble $CF_3SO_2NNa_2$.

Example 7

Excess $CF_3SO_2NH_2$ and NaOH were reacted in water to prepare $CF_3SO_2NNaH$. Water and excess $CF_3SO_2NH_2$ were removed under vacuum (0.1 Pa, $10^{-3}$ Torr) at 70° C.; the residue was dried for 16 h at 0.1 Pa, $10^{-3}$ Torr at 110° C. Following the procedures of Example 1, inside the dry box, a 250 ml two neck round bottom flask with a magnetic siring bar was charged with 1.034 g of the $CF_3SO_2NNaH$. The material was dissolved in 100 ml of anhydrous acetonitrile of Example 1. The procedures of Example 10 were followed but the three necked flask was replaced by the two-necked flask and the thermocouple was omitted. The reaction mixture was stirred at room temperature and the SRAD was inverted thereby feeding the NaH to the solution in the flask. No immediate reaction could be observed. Over the first 150 min, only a total of 10 ml of an evolving gas could be collected. After 150 min, the formation of gas started. Over the next 105 min, additional 135 ml of gas were collected in the graduated cylinder. During this period, the appearance of the reaction mixture changed. The fine residue in the reaction mixture changed to a thicker precipitation that settled easily at the bottom of the flask when the stirring was stopped. The reaction mixture was stirred for another 14 h at room temperature. 10 ml of additional gas were collected during this period. The flask was brought into the dry box and a sample of the solution was submitted for NMR No fluorine could be detected, indicating the complete conversion of $CF_3SO_2NHNa$ into insoluble $CF_3SO_2NNa_2$.

Example 8

Following the procedure of Example 10, inside the dry-box, a 250 ml three neck round bottom flask was charged with 75 ml of anhydrous acetonitrile prepared as in Example 1. 0.189 g NaH was placed in the SRAD. 0.879 g of the $CF_3SO_2NHNa$ of Example 10 was dissolved in 25 ml acetonitrile prepared as in Example 1 and placed in an addition funnel which substituted for the thermocouple of Example 10. After the required connections were made, the reaction mixture was stirred at room temperature and the NaH was immediately added to the solvent. 6 ml of gas were collected over a period of 3 h. The $CF_3SO_2NHNa$ solution was added and the reaction mixture was continued to be stirred at room temperature. 1 h 45 min after the addition of the $CF_3SO_2NHNa$, an additional 4 ml of gas had been collected. The reaction mixture turned slightly yellow. 4 h after the addition of the $CF_3SO_2NHNa$, the reaction seemed to start. 6 h and 40 min after the addition of the monosodium solution, a total of 80 ml of gas since the addition had been collected. The reaction mixture was sired for another 14 h 30 min. A total of 116 ml gas had been collected. 103 ml are the expected amount The flask was brought into the dry-box and an NMR sample was collected from the solution. Only a trace of a fluorine signal at −80.6 ppm could be detected, indicating the conversion of $CF_3SO_2NHNa$ into insoluble $CF_3SO_2NNa_2$.

2.120 g PSEPVE was added to the now bright yellow solution, containing a yellowish solid. The reaction mixture turned orange and after 15 min stirring at room temperature, the reaction mixture turned clear. A fine precipitate formed. An NMR sample was collected after 1 h showing the formation of the product $CF_2=CFOCF_2CF(CF_3)OCF_2CF_2SO_2N(Na)SO_2CF_3$ and excess PSEPVE.

Comparative Example 1

Inside the dry-box of Example 1, a flask was charged with 0.93 g of $CF_3SO_2NHNa$ from Example 11, 0.135 g NaH (Aldrich) and 20 ml of anhydrous THF (Aldrich; distilled off Na metal). The reaction mixture was stirred for 4 h at room temperature and was then filtered through a glass filter (fine porosity). The filtrate was collected in a flask and brought outside the dry-box. All solvents were removed under vacuum (0.1 Pa, $10^{-3}$ Torr) and the residue was heated to 65° C. for 24 h at 0.1 Pa, $10^{-3}$ Torr. 0.862 g (5.04 mmol) of $CF_3SO_2NHNa$ were recovered, corresponding to 92.6% of the staring material. The dried material was brought into the dry-box and 50 ml of anhydrous acetonitrile were added because it is suspected that $CF_3SO_2NNa_2$ is slightly soluble in THF. The majority of the material was dissolved in the acetonitrile and only a slight trace of a solid could be observed in the solution. It was not attempted to separate this residue. It should be safe to assume that less than 10% of the $CF_3SO_2NHNa$ have been converted to $CF_3SO_2NNa_2$ after 4 h in THF at room temperature.

Example 9

Following the procedures of Example 11, inside the dry-box, the round bottom flask was charged with 0.866 g of the $CF_3SO_2NHNa$ of Example 11. The material was dissolved in 100 ml of anhydrous THF (Aldrich; distilled from Na metal; stored over molecular sieves inside the dry-box). 0.171 g of NaH was placed in the SRAD. After the required connections were made according to Example 10, the reaction mixture was stirred at room temperature and the NaH was added to the solution. No obvious reaction could be observed. A total of 113.3 ml of collected hydrogen would represent complete conversion under normalized conditions. The gas collected as a function of time is shown in Table 1.

TABLE 1

| Elapsed time (after addition of NaH) | Gas Collected (ml) | estimated % conversion |
| --- | --- | --- |
| 0 h 45 min | 4 | 3.5 |
| 2 h 30 min | 10 | 8.8 |
| 5 h 45 min | 10 | 8.8 |
| 21 h 45 min | 18 | 15.9 |
| 26 h 15 min | 25 | 22.1 |
| 32 h 45 min | 28 | 24.7 |
| 47 h | 38 | 33.6 |
| 49 h 15 min | 43 | 38.0 |
| 53 h 30 min | 47 | 41.6 |
| 84 h 45 min | 53 | 46.9 |
| 86 h 45 min | 55 | 48.6 |
| 97 h 15 min | 65 | 57.5 |
| 118 h | 78 | 69.0 |
| 122 h 15 min | 85 | 75.2 |
| 139 h 45 min | 110 | 97.3 |
| 142 h | 114 | 100.5 |

The reaction was completed after six days at room temperature. The reaction flask was brought inside the dry-box. 2.511 g PSEPVE was added to the colorless reaction mixture that contained a white solid. After 10 min stirring at room temperature, the reaction mixture turned clear. A fine precipitation formed. An NMR sample was collected after 1 h showing the formation of the product $CF_2$=$CFOCF_2CF(CF_3)OCF_2CF_2SO_2N(Na)SO_2CF_3$ and excess PSEPVE.

Example 10

Following the procedure of Example 11, inside the dry-box, the round bottom flask was charged with 0.633, of the $CF_3SO_2NHNa$ of Example 11. The material was dissolved in 100 ml of anhydrous acetonitrile prepared as in Example 1. 0.103 g of NaH was placed in the SRAD. After the required connections were made, the reaction mixture was stirred and heated by immersing the flask in an oil-bath set at 50° C. The reaction mixture was heated for 2 h and the pressure was allowed to equalize inside the flask. No pressure was released through the bubbler for 30 min. After 2 h of heating, the NaH was added to the solution. No obvious reaction could be observed for 20 min. After 20 min., gas was released from the reaction mixture. Evolution of ca. 83 ml of gas was calculated to correspond to complete conversion.

TABLE 2

| Elapsed time (after addition of NaH) | Gas Collected (ml) |
| --- | --- |
| 0 h 20 min | 0 |
| 0 h 25 min | 25 |
| 0 h 30 min | 71 |
| 0 h 35 min | 85 |
| 1 h 0 min | 91 |

The formation of gas stopped after 1 hour. The gas collection record is shown in Table 2. The reaction mixture was stirred for another hour at 50° C. oil bath temperature with no further accumulation of gas. The reaction flask was brought inside the dry-box and an NMR sample was taken from the clear solution above the white residue. Only a trace of a fluorine signal at −80.6 ppm could be detected in the noise of the NMR spectrum, indicating the conversion of $CF_3SO_2NHNa$ into insoluble $CF_3SO_2NNa_2$.

1.740 g PSEPVE was added to the colorless reaction mixture that contained a white solid. The reaction mixture turned yellow and after 10 min stirring at room temperature, the reaction mixture turned clear. A fine precipitation formed. An NMR sample was collected after 1 h showing the formation of the product $CF_2$=$CFOCF_2CF(CF_3)OCF_2CF_2SO_2N(Na)SO_2CF_3$ and excess PSEPVE.

Example 11

Following the procedure of Example 10, the flask was charged with 1.195 g of the $CF_3SO_2NHNa$ which was dissolved in a mixture of 95 ml of THF and 5 ml of anhydrous acetonitrile. 0.195 g of the NaH were placed in the SRAD. After connection to the remainder of the apparatus of Example 10, the NaH was added to the reactants in the flask. No immediate reaction could be observed. Over the first 1 h, only a total of 4 ml of gas was evolved. Over the next 5 h, only a total of 7 ml of the expected 157 ml. Hydrogen gas had been collected. The reaction mixture was stirred for a total of 25 h at room temperature without further observation. 160 ml of gas were collected during this period. 4.500 g PSEPVE was added to the colorless reaction mixture that contained a white solid. The reaction mixture did not change its color and after 10 min stirring at room temperature, the reaction mixture turned clear. A fine precipitation formed. An NMR sample was collected after 1 h showing the formation of the product $CF_2$=$CFOCF_2CF(CF_3)OCF_2CF_2SO_2N(Na)SO_2CF_3$ and excess PSEPVE.

Example 12

Employing the reagents and equipment of Example 1, inside the dry-box 3.033 g of the sublimed $CF_3SO_2NH_2$ was placed in a round bottom flask and dissolved in 50 ml of the anhydrous acetonitrile. 1.511 g of $CaH_2$ (Aldrich; 90–95%) was added. The reaction mixture was stirred with a magnetic stir bar at room temperature for 48 h. No fluorine could be detected in the reaction mixture after this time period by NMR, indicating the complete conversion of $CF_3SO_2NH_2$ to $(CF_3SO_2NCa)_2$.

9.461 g of distilled PSEPVE was added and the reaction mixture was stirred at room temperature. No conversion to the product could be observed after 24 h at room temperature.

The reaction mixture was heated to 60° C. for 7 days. The reaction mixture was filtered inside the dry-box through a glass filter (medium porosity) and the flask with the collected solution was brought outside the dry-box. All volatiles were removed under vacuum (0.1 Pa, $10^{-3}$ Torr) and the beige residue was heated to 100° C. at 0.1 Pa, $10^{-3}$ Torr for 16 h. $^{19}$F NMR in $CD_3CN$ confirmed the structure $(CF_2$=$CFOCF_2CF(CF_3)OCF_2CF_2SO_2NSO_2CF_3)_2Ca$.

Yield was 1.729 g.

$^{19}$F NMR in $CD_3CN$ $OCF_2^FCF_2^GSO_2NSO_2CF_3^H)_2Ca$: −114.3, −122.7 ppm (A, 1F, A', 1F), −137.3 ppm (B, 1F), −79.5 ppm ($CF_2$, C, 2F), −145.9 ppm (CF, D, 1F), −80.9 ppm ($CF_3$, E, 3F) −85.5 ppm (CF$_2$, F, 2F), −117.6 (CF$_2$, G, 2F), −80.6 ppm (CF$_3$, H, 3F).

MS: Negative electron spray; 573.98, (M-Ca)/2.

Example 13

Inside the dry-box, a round bottom flask was charged with 3.051 g, of the CF$_3$SO$_2$NH$_2$ prepared in the manner of Example 1 and 100 ml of anhydrous acetonitrile prepared as in Example 1. 1.068 g of the NaH (Aldrich) was added slowly over a period of 5 min. The mixture was stirred at room temperature for 26 h inside the dry-box and checked periodically by fluorine NMR until no fluorine could be detected. 3.27 g C$_6$H$_5$SO$_2$F used as received from Aldrich was added to the flask. The reaction mixture thus formed was stirred at room temperature for 144 h. The reaction mixture was centrifuged and all volatiles were removed from the reaction solution. The residue was dried at 110° C. for 24 h at 0.1 Pa, 10$^{-3}$ Torr. The residue was redissolved in 100 ml of anhydrous acetonitrile and filtered through a paper filter. All volatiles were removed from the solution. The residue was dried at 110° C. for 16 h at 0.1 Pa, 10$^{-3}$ Torr. NMR in CD$_3$CN and mass spec. confirmed the structure PhSO$_2$N(Na)SO$_2$CF$_3$.

Yield was 4.284 g.

$^{19}$F NMR in CD$_3$CN: −79.9 ppm (CF$_3$, 3F). $^1$H NMR in CD$_3$CN: 7.90 ppm (2H), 7.54 ppm (3H).

MS: negative electron spray; 288.09, M-Na.

Example 14

As in Example 1, a round bottom flask was charged with 3.082 g of the CF$_3$SO$_2$NH$_2$ prepared as in Example 1 and 100 ml of anhydrous acetonitrile prepared as in Example 1. 1.134 g of the NaH (Aldrich) was added slowly over a period of 5 min. The mixture was stirred at room temperature for 16 h inside the dry-box. No fluorine could be detected by NMR 2.025 g of CH$_3$SO$_2$F (Aldrich, as received) was added. The reaction mixture thus formed was stirred at room temperature for 2 h. The reaction mixture was centrifuged and all volatiles were removed. The residue was dried at 110° C. for 24 h at 0.1 Pa, 10$^{-3}$ Torr. The residue was redissolved in 100 ml of anhydrous acetonitrile and filtered through a paper filter. All volatiles were removed from the solution. The residue was dried at 110° C. for 16 h at 0.1 Pa, 10$^{-3}$ Torr. Yield was 4.20 g.

NMR in CD$_3$CN and mass spec. confirmed the structure CH$_3$SO$_2$N(Na)SO$_2$CF$_3$. $^{19}$F NMR in CD$_3$CN: −79.7 ppm (CF$_3$, 3F). $^1$H NMR in CD$_3$CN: 2.966 ppm (3H). MS: negative electron spray; 226.06, M-Na.

Example 15

A 400 mL Hastelloy autoclave prechilled to <−20° C. was charged with PSEPVE (150 g) and 15 mL of 0.17 M hexafluoropropylene oxide dimer peroxide. The vessel was closed, evacuated, then filter charged with vinylidene fluoride (64 g) and CO$_2$ (150 g), and shaken at room temperature for 18 hr. Excess pressure was released and the viscous residue was analyzed by $^{19}$F NMR (acetone d$_6$) which clearly indicated residual monomer. Estimated conversion of PSEPVE was ca 60%. The entire sample was devolatilized at 100° C. (0.5 mm) for several hours. Sample was a rather tough rubber, deformable by application of force. It did not flow significantly at room temperature under its own weight.

$^{19}$F NMR (acetone d$_6$): +45.5 (s, a=0.91), −77.5 to −79.8 (m, a=7.00), −91 to −95.5 (m, a=4.038), −108 to −115.9 (m, a=4.680), −121.8, −122.3, and −122.8 (series of broadened m's. a=1.651), −124 to −127 (bd m's, a=0.766), −129.5 (s, a=0.0244, assigned to internal CF$_2$ of CF$_3$CF$_2$CF$_2$OCF(CF$_3$)-fragment (end group), −144 (bm, CF from PSEPVE side chains). Integration was consistent with 24.5 mol % PSEPVE. Integration of end groups from dimer peroxide fragments, assuming that all ends are of this type, gives an estimate of M$_n$ for the copolymer as 106,000. $^1$H NMR showed only broad signal 3.5–2.7.

4.47 g of the copolymer so prepared was dried at 0.1 Pa, 10$^{-3}$ Torr for 24 h at 100° C. 100 ml of anhydrous THF was added to the polymer and the reaction mixture was refluxed for 16 h to dissolve the polymer. 1.344 g of the CF$_3$SO$_2$NNa$_2$ prepared in Example 1 were added at room temperature over a period of 2 h. The reaction mixture was stirred at room temperature. The reaction mixture turned cloudy after 3 h. An additional 0.418 g of CF$_3$SO$_2$NNa$_2$ was added over the next 6 days. After all the CF$_3$SO$_2$NNa$_2$ was added, the reaction mixture so formed was heated to 50° C. After 3 days at 50° C., $^{19}$F NMR indicated that the reaction was complete.

The reaction mixture was brought outside the dry-box and centrifuged. A slightly brown solution could be separated from a dark brown residue. Analysis of the residue showed that it was mostly NaF and excess CF$_3$SO$_2$NHNa starting material. All volatiles were removed from the combined solutions and the beige residue was heated to 110° C. at 0.1 Pa, 10$^{-3}$ Torr for 16 h. Yield is 3.8 g. $^{19}$F NMR in d$_8$-THF confirmed complete conversion of the sulfonyl fluoride groups of the polymer to imide. $^{19}$F NMR Residue in d$_8$-THF; −79 to −85 ppm (CF$_3$SO$_2$, CF$_3$(CF), 2×CF$_2$O, 10 F), −90 to −135 ppm (CF$_2$SO$_2$, VF$_2$ fluorines), −146.0 ppm (CF(CF$_3$), 1F); integration gives 28 mol % PSEPVE-imide in the polymer. $^1$H NMR Residue in d$_8$-THF: 2 to 3.8 ppm VF$_2$ protons.

Example 16

CH$_2$=CHCH$_2$CF$_2$CF$_2$OCF$_2$CF$_2$SO$_2$F was synthesized according to the teachings of Guo et al., Huaxue Xuebao (1984), 42(6), 592–5.

As in Example 1, a round bottom flask was charged with 2.02 g of CF$_3$SO$_2$NNa$_2$ prepared as in Example 1 and 60 ml of anhydrous acetonitrile prepared as in Example 1. 3.73 g CH$_2$=CHCH$_2$CF$_2$CF$_2$OCF$_2$CF$_2$SO$_2$F was added drop wise over a period of 5 min. After 20–25 min, the mixture turned clear and then generated a precipitation. The mixture was stirred for 3 h at room temperature. The reaction mixture was filtered through a paper filter inside the dry box. All volatiles were removed and the white residue was heated to 100° C. for 16 h at 0.1 Pa, 10$^{-3}$ Torr. Yield was 3.635 g. $^{19}$F NMR in CD$_3$CN confirmed the structure CH$_2$=CHCH$_2$CF$_2$CF$_2$OCF$_2$CF$_2$SO$_2$N(Na)SO$_2$CF$_3$.

$^{19}$F NMR in CD$_3$CN:

CH$_2$=CHCH$_2$CF$_2$ACF$_2$BOCF$_2$CCF$_2$DSO,N(Na)SO$_2$CF$_3$E: −80.60 ppm (CF$_3$, E, 3F), −82.77 ppm (CF$_2$, C, 2F), −88.90 ppm (CF$_2$, B, 2F), −118.31 ppm (2×CF$_2$, A+D, 4F).

$^1$H NMR in CD$_3$CN: CH$_2$A=CHBCH$_2$CCF$_2$CF$_2$OCF$_2$~: 2.87 ppm (CH$_2$, C, tdt, 2H), 5.26 ppm (CH$_2$, A, 2F) and 5.74 ppm (CH$_2$, B, 1F).

I claim:

1. A process comprising: contacting in a liquid dispersion or solution a composition comprising a metal sulfonyl amide salt represented by the formula:

wherein $R^2$ is aryl, fluoro-aryl, or $XCF_2$— where X is H, halogen, fluorinated or non-fluorinated linear or cyclic alkyl radicals having 1–10 carbons, optionally substituted by one or more ether oxygens, b=1 or 2, M is an alkaline earth where b is 1 or an alkali metal where b is 2;

with a non-polymeric sulfonyl fluoride composition represented by the formula, $$R^1(SO_2F)_m$$

wherein m=1 or 2, where when m=1, $R^1$ is a fluorinated or non-fluorinated, saturated or unsaturated hydrocarbyl radical except perfluoroolefin having 1–12 carbons optionally substituted by one or more ether oxygens, or tertiary amino; or, when m=2, $R^1$ is a fluorinated or non-fluorinated, saturated or unsaturated hydrocarbylene, except perfluoroalkylene, radical having 1–12 carbons optionally substituted by one or more ether oxygens;

or with a polymeric sulfonyl fluoride composition comprising monomer units represented by the formula:

$$-[CZ_2CZ(R^3SO_2F)]-$$

wherein $R^3$ is a diradical selected from the group consisting of fluorinated or non-fluorinated alkenyl, including oxyalkenyl or fluorooxyalkenyl, and each Z is independently hydrogen or halogen, and need not be the same; and, causing them to react to form a non-polymeric imide composition represented by the formula:

$$R^1(SO_2NM_bSO_2R^2)_m$$

or, in the alternative, a polymeric imide composition comprising monomer units represented by the formula, $(-[CZ_2CZ(R^3SO_2N(M)SO_2R^2)]-)y$.

2. The process of claim 1 wherein m=1.

3. The process of claim 1 further comprising an inert, aprotic organic liquid.

4. The process of claim 3 wherein the organic liquid is an ether.

5. The process of claim 4 wherein the ether is tetrahydrofuran.

6. The process of claim 1 wherein $R^2$ is a perfluoroalkyl radical.

7. The process of claim 6 wherein $R^2$ is a trifluoromethyl radical.

8. The process of claim 1 wherein M is an alkali metal, b=2.

9. The process of claim 8 wherein M is sodium.

10. The process of claim 2 wherein $R^1$ is a perfluorovinyl ether radical.

11. The process of claim 10 wherein the perfluorovinyl ether radical is represented by the formula:

$$CF_2=CF-O-[CF_2CF(R^4)-O_z]_a-CF_2CF_2-$$

wherein $R^4$ is F or perfluoroalkyl having 1–4 carbons, z=0 or 1, and a=0–3.

12. The process of claim 11 wherein $R^4$ is trifluoromethyl, z=1, and a=0 or 1.

13. The process of claim 1 wherein Z is F.

14. The process of claim 1 wherein $R^3$ is a perfluorooxyalkenyl radical.

15. The process of claim 14 where $R^3$ is a perfluorooxyalkenyl radical represented by the formula:

$$-O-[CF_2CF(R^4)-O_z]_a-CF_2CF_2-$$

wherein $R^4$ is F or perfluoroalkyl having 1–4 carbons, z=0 or 1, and a=0–3.

16. The process of claim 15 wherein $R^4$ is trifluoromethyl, z=1, and a=0 or 1.

17. The process of claim 1 wherein the sulfonyl fluoride polymer composition further comprises comonomer units derived from the group consisting of fluorinated, but not perfluorinated, olefins, non-fluorinated olefins, fluorinated vinyl ethers, non-fluorinated vinyl ethers, and mixtures thereof.

18. The process of claim 17 wherein the comonomer units are derived from the group consisting of ethylene, perfluoroalkyl vinyl ether, vinylidene fluoride, and vinyl fluoride, and mixtures thereof.

19. The process of claim 18 wherein the comonomer units comprise vinylidene fluoride.

20. The process of claim 19 wherein the vinylidene fluoride is at a concentration of at least 50 mol % in the sulfonyl fluoride polymer composition.

21. The process of claim 1 wherein the monomer units represented by the formula $-[CZ_2CZ(R^3SO_2F)]-$ are present in the sulfonyl fluoride polymer at a concentration of up to 50 mol %.

22. The process of claim 21 wherein the monomer units represented by the formula $-[CZ_2CZ(R^3SO_2F)]-$ are present in the sulfonyl fluoride polymer at a concentration of up to 20 mol %.

23. The process of claim 9 further comprising the step of performing an ion exchange to form the lithium imide.

24. The process of claim 23 wherein the ion exchange is performed by contacting the sodium imide with organic lithium chloride solution.

25. The process of claim 1 wherein the composition comprising the dimetal sulfonyl amide salt comprises at least 50 mol % of said dimetal sulfonyl amide salt.

26. The process of claim 25 wherein the composition comprises at least 90 mol % of said dimetal sulfonyl amide salt.

27. The process of claim 1 wherein the dimetal sulfonyl amide salt is contacted with the non-polymeric sulfonyl fluoride composition causing them to react to form the non-polymeric imide composition.

28. The process of claim 1 wherein the dimetal sulfonyl amide salt is contacted with the polymeric sulfonyl fluoride composition causing them to react to form the polymeric imide composition.

29. The process of claim 18 wherein the sulfonyl fluoride polymer composition further comprises a termonomer unit derived from a perfluoro-olefin.

30. The process of claim 29 wherein the perfluorolefin is tetrafluoroethylene, hexafluoropropylene or a combination thereof.

* * * * *